United States Patent
Arnaud et al.

(10) Patent No.: US 9,603,783 B2
(45) Date of Patent: Mar. 28, 2017

(54) THREE-PHASE COSMETIC COMPOSITIONS COMPRISING NACRES

(71) Applicant: L'OREAL, Paris (FR)

(72) Inventors: Pascal Arnaud, L'Hay les Roses (FR); Sylvie Gineston, St. Mauer des Fosses (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/779,066

(22) PCT Filed: Mar. 26, 2014

(86) PCT No.: PCT/EP2014/056025
§ 371 (c)(1),
(2) Date: Sep. 22, 2015

(87) PCT Pub. No.: WO2014/154732
PCT Pub. Date: Oct. 2, 2014

(65) Prior Publication Data
US 2016/0051454 A1   Feb. 25, 2016

(30) Foreign Application Priority Data

Mar. 26, 2013  (FR) ...................... 13 52727
Mar. 26, 2013  (FR) ...................... 13 52735

(51) Int. Cl.
| | | |
|---|---|---|
| *A61Q 19/00* | (2006.01) |
| *A61K 8/03* | (2006.01) |
| *A61Q 5/08* | (2006.01) |
| *A61K 8/26* | (2006.01) |
| *A61K 8/37* | (2006.01) |
| *A61Q 1/00* | (2006.01) |
| *A61Q 5/00* | (2006.01) |
| *A61K 8/19* | (2006.01) |
| *A61K 8/02* | (2006.01) |
| *A61K 8/25* | (2006.01) |
| *A61K 8/29* | (2006.01) |
| *A61Q 1/02* | (2006.01) |

(52) U.S. Cl.
CPC .............. *A61K 8/03* (2013.01); *A61K 8/0262* (2013.01); *A61K 8/19* (2013.01); *A61K 8/25* (2013.01); *A61K 8/26* (2013.01); *A61K 8/29* (2013.01); *A61K 8/37* (2013.01); *A61Q 1/00* (2013.01); *A61Q 1/02* (2013.01); *A61Q 5/00* (2013.01); *A61Q 5/08* (2013.01); *A61Q 19/00* (2013.01); *A61K 2800/412* (2013.01); *A61K 2800/413* (2013.01); *A61K 2800/436* (2013.01); *A61K 2800/621* (2013.01)

(58) Field of Classification Search
CPC ............ A61Q 19/00; A61Q 1/02; A61Q 5/08
See application file for complete search history.

(56) References Cited

U.S. PATENT DOCUMENTS

2004/0223929 A1* 11/2004 Clapp .................. A61K 8/0237
                                                                      424/63
2004/0223991 A1    11/2004 Wei et al.
2008/0261844 A1* 10/2008 Ruppert .................. A61K 8/03
                                                                      510/158

FOREIGN PATENT DOCUMENTS

| EP | 1 230 907 A1 | 8/2002 |
|---|---|---|
| EP | 1 927 335 A1 | 6/2008 |

* cited by examiner

*Primary Examiner* — Carlos Azpuru
(74) *Attorney, Agent, or Firm* — Polsinelli PC

(57) ABSTRACT

This invention relates to a cosmetic composition comprising a physiologically acceptable medium containing aqueous phase, an oily phase and nacre particles, constituted of a substrate partially or totally coated with one or more layers.

20 Claims, No Drawings

THREE-PHASE COSMETIC COMPOSITIONS COMPRISING NACRES

CROSS REFERENCE TO RELATED APPLICATIONS

This application is a National Phase filing under 35 U.S.C. § 371 of PCT/EP2014/056025filed on Mar. 26, 2014; and this application claims priority to Application No. 13 52735filed in France on Mar. 26, 2013; and this application claims priority to Application No. 13 52727 filed in France on Mar. 26, 2013. The entire contents of each application are hereby incorporated by reference.

This invention has for object three-phase cosmetic compositions, in particular for makeup and/or care, comprising specific nacres. More particularly, this invention has for object compositions comprising an oily phase, an aqueous phase and nacre particles that have the form of three superposed layers at rest.

It is known by those skilled in the art to use nacres in makeup, care or hair care products, in order to provide optical effects of color and shine on the skin, lips, eyelashes, nails or on hair.

In order to enhance these nacres, they can simply be dispersed in a single liquid phase, transparent or translucent which has a visually attractive aspect, characterized by the movement of the nacres in the medium, when the product is shaken.

These nacres can as such be conveyed in an oily phase, because they disperse well in this medium and they have little tendency to agglomerate. There are as such products on the marked comprised solely of an oily liquid phase in which the nacres are dispersed and which have for function to illuminate the skin or the hair.

The substantial quantity of oils can however limit the color effect after application on the skin or hair, especially if the oils are not volatile and the sensory properties can be degraded in particular in terms of freshness, greasy and sticky feeling.

In order to avoid these disadvantages, the nacres can be conveyed in an aqueous liquid medium, but in this case a strong tendency to agglomerate is observed, which manifests itself in particular when the product is at rest. A compact layer is then formed coming from the sedimentation and settling of nacres, which are difficult to disperse via shaking.

Moreover, a simple aqueous medium does not make it possible to obtain satisfactory sensory properties in particular in terms of application and comfort properties over time.

In addition, when the product is again at rest, it is most often observed that a portion of the nacres adheres along the walls of the bottle above the liquid, which decreases its aesthetic aspect.

This defect is particularly visible when the filling of the bottle by the liquid is only partial and that the walls of the bottle are made of glass. It is therefore desirable to find nacres that do not have this disadvantage and that remain confined in the liquid medium after shaking.

It therefore remains necessary to search for a means of obtaining a dispersion of nacres in a liquid medium, transparent or translucent, that does not have the phenomenon of agglomeration at rest, and which leads to a product that has good properties in terms of application, freshness and comfort over time.

It therefore also remains necessary to search for a means of obtaining a dispersion of nacres in a liquid medium, transparent or translucent, that does not have the phenomenon of adherence of the nacres on the walls of the container containing said dispersion, and which leads to a product that has good properties in terms of application, freshness and comfort over time.

This invention therefore has for purpose to provide a cosmetic composition comprising nacres that has properties of application, freshness and comfort over time that are satisfactory.

This invention also has for purpose to provide a cosmetic composition comprising nacres that has an attractive visual aspect.

This invention also has for purpose to provide a cosmetic composition comprising nacres that has satisfactory properties of rehomogenizing and which at rest has three visually separate phases.

This invention also has for purpose to provide a cosmetic composition, transparent or translucent, that does not have the phenomenon of agglomeration of nacres at rest.

This invention also has for purpose to provide a cosmetic composition, transparent or translucent, comprising nacres that settle in the aqueous phase without adhering to the walls of the container containing them.

As such, this invention relates to a cosmetic composition comprising a physiologically acceptable medium containing:

(1) an aqueous phase;
(2) an oily phase with a density less than that of the aqueous phase; and
(3) nacre particles, dispersed in the aqueous phase, constituted of a substrate partially or totally coated with one or more layers, with at least one of the layers being a layer of metal oxide, said nacre particles being chosen from the following particles:

either nacre particles (P1) of which the average size is between 2 µm and 1,000 µm, wherein the substrate is mica or alumina, said particles do not comprise a silica layer on the surface, and with the reserve that, when the layer of metal oxide comprises more than 30% by weight of titanium oxide with respect to the total weight of the particles, the average size of said particles is between 2 µm and 20 µm;

or nacre particles (P2) wherein the substrate is chosen from the comprising silica, borosilicate, mica and alumina, and when the substrate is mica or alumina, the nacre particles comprise a layer of silica on the surface, and when the metal oxide is an iron oxide, the iron oxide content is less than 50% by weight with respect to the total weight of the particles, said cosmetic composition comprising from 5% to 85% by weight of oily phase with respect to the total weight of said composition.

Unexpectedly, it was found by the inventors that it is possible to obtain a product that meets the criteria sought concerning the properties of application, freshness and comfort over time and which has an attractive visual aspect, by dispersing specific nacres in an aqueous phase in the presence of an oily phase that is incompatible with this aqueous phase.

When the product is at rest, it has the form of three separate superposed layers, with the oily phase constituting the upper layer, the aqueous phase the intermediate layer and the nacres the lower layer. Under shaking, the three layers intimately mix to form a homogeneous product which can then be applied.

The compositions according to the invention are therefore three-phase compositions at rest, wherein the nacres remain confined in the liquid medium after shaking.

According to an embodiment, this invention relates to a cosmetic composition comprising a physiologically acceptable medium containing:
(1) an aqueous phase;
(2) an oily phase with a density less than that of the aqueous phase; and
(3) nacre particles (P1), dispersed in the aqueous phase, constituted of a substrate partially or totally coated with one or more layers, the average size of said particles being between 2 µm and 1,000 µm,
said substrate being mica or alumina,
at least one of the layers being a layer of metal oxide,
said particles (P1) do not comprise a silica layer on the surface, and
with the reserve that, when the layer of metal oxide comprises more than 30% by weight of titanium oxide with respect to the total weight of the particles, the average size of said particles is between 2 µm and 20 µm,
said cosmetic composition comprising from 5% to 70% by weight of oily phase with respect to the total weight of said composition.

According to this embodiment, at rest, the aqueous and oily phases separate progressively and the nacres settle in the aqueous phase in order to form a layer which can easily be redispersed by shaking the product again.

According to another embodiment, this invention relates to a cosmetic composition comprising a physiologically acceptable medium containing:
(1) an aqueous phase;
(2) an oily phase with a density less than that of the aqueous phase; and
(3) nacre particles (P2), dispersed in the aqueous phase, constituted of a substrate partially or totally coated with one or more layers,
at least one of the layers being a layer of metal oxide, and
said substrate being chosen from the group comprising silica, borosilicate, mica and alumina,
wherein, when the substrate is mica or alumina, the nacre particles (P2) comprise a layer of silica on the surface, and
when the metal oxide is an iron oxide, the iron oxide content is less than 50% by weight with respect to the total weight of the particles,
said cosmetic composition comprising from 5% to 85% by weight of oily phase with respect to the total weight of said composition.

According to this embodiment, at rest, the aqueous and oily phases separate progressively and the nacres settle in the aqueous phase without adhering to the walls of the bottle containing them.

Nacres

The cosmetic compositions according to the invention comprise nacre particles, dispersed in the aqueous phase, with these particles able to be identical or different. The compositions according to the invention may thus comprise mixtures of nacre particles of different types.

In the framework of this invention, "nacres" is understood to mean colored particles of any form, whether or not iridescent, which have an effect of color via optical interference.

These nacre particles have the form of a dispersion of particles in the aqueous phase, and, as indicated hereinabove, once the composition is shaken, the latter form with the aqueous and oily phases a homogeneous product, easy to apply on keratin surfaces, in particular on the skin or hair.

According to an embodiment, the nacres are present in the composition of the invention in a quantity of active material ranging from 0.1% to 30% by weight, preferably from 0.5% to 20% by weight and even more preferentially from 2% to 15% by weight, with respect to the total weight of said composition.

The nacre particles according to the invention are composite particles, constituted of several materials. The particles can be of a varied form, for example in platelet and lamellar form.

According to the invention, the nacres have a multilayer structure constituted a natural or synthetic substrate.

The nacre particles used in the framework of the invention comprise a substrate that is coated with one or more layers of a material different from the substrate. These particles are therefore constituted of several materials.

They as such comprise a base layer which corresponds to the substrate where on at least one layer of another material is superposed. The substrate according to the invention can be covered with one, two or three separate layers of a different nature.

The substrate of the nacre particles can be partially coated with at least one layer of another material. Within the scope of this invention, the term "partially coated" denotes that the substrate is coated with at least one layer at a rate of 50% to 99.9% of the surface of said substrate.

According to an embodiment, the substrate of the nacre particles is totally coated with at least one layer of another material. This embodiment corresponds to the case where the entire external surface of the substrate, namely the surface coated with at least one layer, is covered by said layer.

In the framework of this invention, the nacre particles are defined by their average size which is measured by granulometry. The average size of the nacres corresponds to their apparent diameter because they are assimilated, during the measurement, to spheres. The average size is characterized by $D_{50}$ which corresponds to the average granulometry of half of the population.

The measurement of the granulometry is taken in the following way: 0.1 g of nacre are introduced into a bottle of 12 to 14 g of isopropyl myristate. The sample is shaken until a complete dispersion is obtained then the granulometry of the nacres is measured in this medium using the Mastersizer 2000 of the Malvern company.

According to an embodiment, the nacre particles of the invention (P1) can comprise titanium dioxide as a metal oxide. According to this embodiment, when the content of titanium dioxide is less than or equal to 30%, the nacre particles have an average size that can vary from 2 µm to 1,000 µm, preferably from 3 µm to 500 µm and even more preferentially from 5 µm to 250 µm.

According to this embodiment, when the content of titanium dioxide is greater than 30%, the nacre particles (P1) have an average size that can vary from 2 µm to 20 µm, preferably from 3 µm to 15 µm and even more preferentially from 5 µm to 12 µm.

The contents mentioned for the titanium dioxide correspond to percentages by weight of titanium dioxide with respect to the total weight of the nacre particles.

According to this embodiment, the nacre particles (P1) are constituted of mica or alumina as a substrate. Preferably, this substrate is natural or synthetic mica.

The nacre particles (P2) according to the invention preferably have an average size that can vary from 2 µm to 1,000

µm, preferably from 3 µm to 500 µm and even more preferentially from 5 µm to 250 µm.

According to an embodiment, the nacre particles (P2) of the invention can comprise iron dioxide as a metal oxide. According to the invention, when the substrate of particles (P2) is coated with one or more layers of iron oxide, the total content of these layers must be less than or equal to 50%.

According to an embodiment, the substrate of the nacre particles (P2) according to the invention is a synthetic substrate chosen from silica or borosilicate. Preferably, the substrate is borosilicate.

According to another embodiment, the substrate of the nacre particles (P2) according to the invention is a synthetic substrate chosen from mica and alumina. According to this embodiment, the nacre particles (P2) then necessarily comprise silica as the most external layer.

As such, when the substrate of the particles (P2) is mica or alumina, the particles (P2) comprise a layer of silica and this layer is located on the surface of said particles. This is then the most external layer of said particles, i.e. this layer of silica must not be covered with another layer.

Among the layers that cover the substrate of particles (P1) or (P2), at least one is a layer of metal oxide. According to an embodiment, the metal oxides are chosen from the group comprising titanium oxide, iron oxides, chromium oxides, tin oxides, alumina oxides and mixtures thereof.

As such, the substrate is at least partially coated with at least one layer chosen for example from titanium oxide, iron oxides in particular $Fe_2O_3$, tin, chromium and alumina.

According to an embodiment, the substrate of particles (P1) or (P2) is coated with a single layer of metal oxide or several separate layers of metal oxide.

In particular, the nacre particles (P1) or (P2) according to the invention are comprised of the substrate covered with a single layer of metal oxide, or with two or three different layers of metal oxide.

According to an embodiment, the nacre particles (P1) according to the invention comprise at least one layer of iron oxide.

According to an embodiment, the nacre particles (P1) according to the invention comprise at least one layer of titanium oxide.

According to an embodiment, the nacre particles (P1) according to the invention comprise at least one layer of iron oxide and at least one layer of titanium oxide.

According to the invention, the substrate of particles (P1) or (P2) can also be coated furthermore with at least one layer comprised of bismuth oxychloride, ultramarine blue, Prussian blue, manganese violet, cochineal carmine and mixtures thereof.

The particles according to the invention (P1) or (P2) can therefore comprise, in addition to at least one layer of metal oxide, an additional layer such as defined hereinabove.

The particles (P1) according to the invention may also further comprise at least one layer of silica. According to this embodiment, this layer of silica must not be located on the surface of said particles. It must therefore not be the most external layer of said particles. If the nacre particles (P1) according to the invention comprise a layer of silica, the latter must be covered with another layer for example a layer of metal oxide.

For the purposes of illustration nacres (P1) that can be implemented in the framework of this invention, mention can in particular be made of the nacres marketed by BASF Personal Care Ingredients in the ranges: Flamenco, Timica, Cloisonne, Cosmica, Gemtone and Chroma-lite; the nacres marketed by MERCK in the ranges: Timiron, Colorona and Microna and the nacres marketed by SUDARSHAN CHEMICAL in the range Pearlescent Pigment Prestige.

According to an embodiment, the nacre particles (P2) according to the invention comprise silica or borosilicate as a substrate and at least two layers of metal oxide, and preferably a layer of titanium oxide and layer of tin oxide.

According to an embodiment, the nacre particles (P2) according to the invention comprise mica as a substrate.

According to an embodiment, the nacre particles (P2) according to the invention comprise mica as a substrate, one or two layers of metal oxide and silica as an external layer.

For the purposes of information nacres (P2) that can be implemented in the framework of this invention, mentioned can in particular be made of nacres marketed by BASF Personal Care Ingredients under the name of Reflecks Gilded Gold G232L; nacres marketed by MERCK under the name of Timiron Splendid Red and Timiron Artic Silver, under the name of Colorona Precious Gold, Xirona Magic Mauve, and Ronastar Gold, and nacres marketed by NIPPON SHEET GLASS under the name of Metashine MC 1080RR and Microglass Metashine MC 2080 PSS 1.

Aqueous Phase

The cosmetic compositions according to the invention comprise an aqueous phase wherein the nacre particles are dispersed.

According to one embodiment, the aqueous phase comprises 5% to 80%, particularly 10% to 80%, by water weight in relation to the total weight of the composition.

More particularly, this aqueous phase can comprise 10% to 60%, particularly 15% to 60%, by water weight in relation to the total weight of the composition.

According to one embodiment, when the nacre particles are particles (P1) according to the invention, the aqueous phase comprises 5% to 80%, particularly 10% to 60%, by water weight in relation to the total weight of the composition.

According to one embodiment, when the nacre particles are particles (P2) according to the invention, the aqueous phase comprises 10% to 80%, particularly 15% to 60%, by water weight in relation to the total weight of the composition.

The water suitable for the invention can also be a natural spring water or a floral water. In particular, a water suitable for the invention may be a floral water such as cornflower water and/or a mineral water such as VITTEL water, LUCAS water or LA ROCHE POSAY water and/or a spring water.

According to an embodiment, the aqueous phase of the compositions of the invention can further comprise at least one organic solvent miscible in water.

This organic solvent, miscible in water, can be chosen from:
- mono-alcohols having 1 to 8 carbon atoms, and in particular 2 to 5 carbon atoms, such as ethanol and isopropanol,
- glycols comprising 2 to 8 carbon atoms, such as propylene glycol, butylene glycol, pentylene glycol, hexylene glycol, dipropylene glycol and caprylylglycol,
- polyethylene glycols,
- polyhydric alcohols having 2 to 8 carbon atoms such as glycerol, and
- mixtures of the latter.

In particular, the aqueous phase of the compositions of the invention can comprise ethanol, propylene glycol, glycerol, or a mixture of the latter. According to an embodiment, the aqueous phase comprises, in addition to water, a mixture of ethanol, propylene glycol and glycerol.

The aqueous phase can also contain any water-soluble or water-dispersible compound compatible with an aqueous phase. Among these compounds, active substances, coloring agents, salts such as sodium chloride and magnesium sulfate, gelling agents, preservatives and any other water-soluble additive commonly used in cosmetic products can be mentioned.

Oily Phase

The compositions according to the invention also comprise an oily phase of which the density is less than that of the aqueous phase. As such, at rest, the oily phase is above the aqueous phase and constitutes the upper layer of the composition according to the invention.

The density according to the invention corresponds to the density at ambient temperature.

According to one embodiment, the oily phase represents 5% to 85%, in particular 5% to 70%, preferably 20% to 70%, in particular 20% to 60%, and preferentially 30% to 60%, in particular 30% to 50%, by weight in relation to the total weight of said composition.

According to one embodiment, when the nacre particles are particles (P1) according to the invention, the oily phase represents 5% to 70%, preferably 20% to 60%, and preferentially 30% to 50%, by weight in relation to the total weight of the composition.

According to one embodiment, when the nacre particles are particles (P2) according to the invention, the oily phase represents 5% to 85%, preferably 20% to 70%, and preferentially 30% to 60%, by weight in relation to the total weight of the composition.

The oily phase (or fat phase) of the compositions according to the invention comprises at least one oil. It may consist of a single oil or a mixture of a plurality of oils. The term "oil" is intended to mean any fatty substance in liquid form at ambient temperature (20-25° C.) and at atmospheric pressure. These oils may be of animal, plant, mineral or synthetic origin.

According to one embodiment, the oils are chosen from the group consisting of hydrocarbon oils, silicone oils, fluorinated oils and mixtures thereof.

According to the present invention, the term "hydrocarbon oil" denotes an oil containing mainly hydrogen and carbon atoms.

The term "silicone oil" denotes an oil comprising at least one silicon atom and particularly comprising at least one Si—O group.

The term "fluorinated oil" denotes an oil comprising at least one fluorine atom.

The oils may optionally comprise oxygen, nitrogen, sulfur and/or phosphorus atoms, for example in the form of hydroxyl or acid radicals According to one embodiment, the oily phase of the compositions according to the invention comprises at least one volatile oil and/or at least one non-volatile oil.

Volatile Oils

According to one embodiment, the oily phase of the compositions according to the invention comprises at least one volatile oil. The oily phase of the compositions according to the invention may comprise a mixture of a plurality of volatile oils.

The term "volatile oil" is intended to mean any non-aqueous medium capable of evaporating on contact with the skin or the lips, in less than one hour, at ambient temperature and at atmospheric pressure. The volatile oil is a volatile cosmetic oil that is liquid at ambient temperature. More precisely, a volatile oil has an evaporation rate of between 0.01 and 200 mg/cm$^2$/min, inclusive.

To measure this evaporation rate, 15 g of oil or an oil mixture to be tested are introduced into a crystallizer with a diameter of 7 cm, placed on a scale located in a large chamber of around 0.3 m$^3$ with controlled temperature, at 25° C., and hygrometry, at 50% relative humidity. The liquid is left to evaporate freely, without stirring, by allowing ventilation with a fan (PAPST-MOTOREN, reference 8550 N, rotating at 2700 rpm) arranged vertically above the crystallizer containing said oil or said mixture, with the blades being directed toward the crystallizer and at a distance of 20 cm with respect to the crystallizer base. The mass of oil remaining in the crystallizer is measured at regular intervals. The evaporation rates are expressed in mg of oil evaporated per unit of surface (cm$^2$) and per unit of time (minutes).

The volatile oils may be hydrocarbon, silicone or fluorinated oils.

The volatile oils may be chosen from hydrocarbon oils having 8 to 16 carbon atoms, and particularly branched $C_8$-$C_{16}$ alkanes (also known as isoparaffins or isoalkanes), such as isododecane (also known as 2,2,4,4,6-pentamethylheptane), isodecane, isohexadecane, and, for example, the oils sold under the trade names ISOPARS® or PERMETHYLS®.

As hydrocarbon volatile oils, mention may also be made of linear $C_9$-$C_{17}$ alkanes, such as dodecane ($C_{12}$) and tetradecane ($C_{14}$), marketed respectively under the references PARAFOL® 12-97 and PARAFOL® 14-97 (Sasol) and such as the alkanes obtained according to the method described in the international application WO2007/068371 A1, such as the mixture of undecane ($C_{11}$) and tridecane ($C_{13}$) marketed under the reference CETIOL® UT (Cognis).

It is also possible to use, as volatile oils, volatile silicones, such as, for example, volatile linear or cyclic silicone oils, in particular those having a viscosity below or equal to 8 centistokes (cst) ($8 \times 10^{-6}$ m$^2$/s), and having, in particular, 2 to 10 silicon atoms, and in particular, 2 to 7 silicon atoms, these silicones optionally comprising alkyl or alkoxyl groups having 1 to 10 carbon atoms. It is possible to cite, as a volatile silicone oil that can be used in the invention, in particular, dimethicones with a viscosity of 5 and 6 cst, octamethyl cyclotetrasiloxane, decamethyl cyclopentasiloxane, dodecamethyl cyclohexasiloxane, heptamethyl hexyltrisiloxane, heptamethyloctyl trisiloxane, hexamethyl disiloxane, octamethyl trisiloxane, decamethyl tetrasiloxane, dodecamethyl pentasiloxane, and mixtures thereof.

More specifically, as a volatile silicone oil, mention may be made of linear or cyclic silicone oils having 2 to 7 silicon atoms, these silicones optionally comprising alkyl or alkoxyl groups having 1 to 10 carbon atoms.

Among the volatile silicone oils, dodecamethyl pentasiloxane is preferred.

Mention may be made, as a volatile fluorinated oil, for example, of nonafluoromethoxybutane or perfluoromethylcyclopentane, and mixtures thereof.

Non-volatile Oils

According to one embodiment, the oily phase of the compositions according to the invention comprises at least one non-volatile oil. The oily phase of the compositions according to the invention may comprise a mixture of a plurality of non-volatile oils.

The term "non-volatile oil" denotes an oil remaining on the skin or keratin fiber at ambient temperature and atmospheric pressure. More precisely, non-volatile oil has an evaporation rate strictly below 0.01 mg/cm$^2$/min. The non-volatile oils may, in particular, be chosen from non-volatile hydrocarbon, fluorinated and/or silicone oils.

As a non-volatile hydrocarbon oil, mention may be made of:

hydrocarbon oils of animal origin, such as perhydrosqualene, hydrocarbon oils of plant origin, such as phytostearyl esters, for instance phytostearyl oleate, phytostearyl isostearate and lauroyl/octyldodecyl/phytostearyl glutamate (AJINOMOTO, ELDEW PS203), triglycerides constituted of glycerol and fatty acid esters, in particular in which the fatty acids may have chain lengths ranging from $C_4$ to $C_{36}$, and in particular from $C_{18}$ to $C_{36}$, these oils may be linear or branched, saturated or unsaturated; these oils may in particular be heptanoic or octanoic triglycerides, shea oil, alfalfa oil, poppy seed oil, pumpkin oil, millet oil, barley oil, quinoa oil, rye oil, candlenut oil, passionflower oil, shea butter, aloe oil, sweet almond oil, peach kernel oil, groundnut oil, argan oil, avocado oil, baobab oil, borage oil, broccoli oil, calendula oil, camelina oil, canola oil, carrot oil, safflower oil, hemp oil, rapeseed oil, cotton seed oil, coconut oil, pumpkin seed oil, wheat germ oil, jojoba oil, lily oil, macadamia oil, corn oil, meadowfoam oil, St. John's Wort oil, monoi oil, hazelnut oil, apricot kernel oil, walnut oil, olive oil, evening primrose oil, palm oil, blackcurrant seed oil, kiwi seed oil, grape seed oil, pistachio oil, pumpkin squash oil, winter squash oil, musk rose oil, sesame oil, soybean oil, sunflower oil, castor oil and watermelon oil, and mixtures thereof, or alternatively caprylic/capric acid triglycerides, such as those sold by STEARINERIE DUBOIS or those sold under the names MIGLYOL 810®, 812® and 818® by DYNAMIT NOBEL, linear or branched hydrocarbons of mineral or synthetic origin, such as liquid paraffins and derivatives thereof, petroleum jelly, polydecenes, polybutenes, hydrogenated polyisobutene such as Parleam;

synthetic ethers having from 10 to 40 carbon atoms;

synthetic esters, such as the oils having the formula $R_1COOR_2$, wherein $R_1$ represents a linear or branched fatty acid residue comprising 1 to 40 carbon atoms, and $R_2$ represents a hydrocarbon chain, particularly branched containing 1 to 40 carbon atoms provided that the sum of the number of carbon atoms of the chains $R_1$ and $R_2$ is greater than or equal to 10. The esters may particularly be chosen from fatty alcohol and acid esters, such as for example: Icetostearyl octanoate, isopropyl alcohol esters, such as isopropyl myristate, isopropyl palmitate, ethyl palmitate, 2-ethylhexyl palmitate, isopropyl stearate or isostearate, isostearyl isostearate, octyl stearate, hydroxylated esters, such as isostearyl lactate, octyl hydroxystearate, diisopropyl adipate, heptanoates, particularly isostearyl heptanoate, alcohol or polyalcohol octanoates, decanoates or ricinoleates, such as propylene glycol dioctanoate, cetyl octanoate, tridecyl octanoate, 2-ethylhexyl 4-diheptanoate and palmitate, alkyl benzoate, polyethylene glycol diheptanoate, propylene glycol 2-diethylhexanoate, and mixtures thereof, $C_{12}$-$C_{15}$ alkyl benzoates, hexyl laurate, neopentanoic acid esters, such as isodecyl neopentanoate, isotridecyl neopentanoate, isostearyl neopentanoate, or octyldodecyl neopentanoate, isononanoic acid esters, such as isononyl isononanoate, isotridecyl isononanoate and octyl isononanoate, hydroxylated esters such as isostearyl lactate and diisostearyl malate;

fatty alcohols that are liquid at ambient temperature, with a branched and/or unsaturated carbon chain having 12 to 26 carbon atoms, such as 2-octyldodecanol, isostearyl alcohol, oleic alcohol, 2-hexyldecanol, 2-butyloctanol and 2-undecylpentadecanol;

$C_{12}$-$C_{22}$ higher fatty acids, such as oleic acid, linoleic acid, linolenic acid, and mixtures thereof;

dialkyl carbonates, the two alkyl chains may be identical or different, such as dicaprylyl carbonate marketed under the name CETIOL CC®, by COGNIS;

fluorinated oils optionally partially hydrocarbon-based and/or silicone-based, such as fluorosilicone oils, fluorinated polyethers or fluorinated silicones, as described in document EP-A-847 752;

silicone oils, such as polydimethylsiloxanes (PDMS) which are non-volatile and linear or cyclic; polydimethylsiloxanes comprising alkyl, alkoxy or phenyl groups which are pendant or at the end of the silicone chain, said groups having from 2 to 24 carbon atoms; phenylated silicones, such as phenyl trimethicones, phenyl dimethicones, phenyltrimethylsiloxydiphenyl-siloxanes, diphenyl dimethicones, diphenylmethyldiphenyl-trisiloxanes or (2-phenylethyl)trimethylsiloxysilicates; and mixtures thereof.

Among the linear or branched hydrocarbons, of mineral or synthetic origin, paraffin oils or petroleum jelly are preferably used.

Among the hydrocarbon oils of plant origin, mention may be made, preferably, of plant oils, such as sweet almond oil, jojoba oil or macadamia nut oil.

According to one embodiment, the oily phase comprises at least one non-volatile hydrocarbon oil. Preferably, this non-volatile hydrocarbon oil is chosen from liquid fatty alcohols at ambient temperature and synthetic esters such as defined hereinabove, as well as mixtures thereof.

According to one embodiment, the oily phase comprises isononyl isononanoate.

According to one embodiment, the oily phase comprises octyldodecanol.

According to one embodiment, the oily phase comprises at least one volatile silicone oil. Preferably, this volatile silicone oil is dodecamethylpentasiloxane.

The oily phase is preferably limpid and transparent.

The oily phase can also contain any liposoluble compound. Among these liposoluble compound, mention can be made of perfumes, coloring agents, active substances, or gelling agents.

Physiologically Acceptable Medium

Other than the compounds indicated hereinabove, namely the aqueous phase, the oily phase and the nacre particles, a composition according to the invention comprises a physiologically acceptable medium.

The term "physiologically acceptable medium" is intended to denote a medium that is particularly suitable for the application of a composition of the invention to the skin, hair or the lips.

The physiologically acceptable medium is generally suitable for the nature of the support to which the composition should be applied, and also for the way in which the composition is to be packaged.

Dyes

The compositions of the invention can also comprise, in addition to nacre particles, an additional dye or a mixture of additional dyes.

According to a preferred embodiment, the content in additional dyes ranges from 0% to 1% by weight, in particular from 0.0001% to 0.5% by weight, with respect to the total weight of said composition.

According to one embodiment, the compositions according to the invention comprise at least one coloring agent. They can comprise a coloring agent or a mixture of several coloring agents, with these coloring agents able to be present in the aqueous and/or oily phase.

According to an embodiment, the compositions according to the invention comprise a coloring agent in the aqueous phase and another coloring agent in the oily phase.

The term "colorants" refers to generally organic compounds soluble in fats such as oils or in a hydroalcoholic phase.

The cosmetic composition according to the invention may also therefore comprise water-soluble or liposoluble coloring agents.

The liposoluble colorants are, for example, Sudan Red, DC Red 21, DC Red 27, DC Green 6, 6-carotene, soybean oil, Sudan Brown, DC Yellow 11, DC Violet 2, DC Orange 5, and Quinoline Yellow.

The water-soluble coloring agents are, for example, beetroot juice and caramel, or coloring agents DC Red 4, DC Red 6, DC Red 22, DC Red 28, DC Red 30, DC Red 33, DC Orange 4, FDC Yellow 5, FDC Yellow 6, DC Yellow 8, FDC Green 3, DC Green 5 and FDC Blue 1.

Additives

A cosmetic composition according to the invention may also further comprise any additive normally used in the field in question, for example selected from gums, anionic, cationic, amphoteric or nonionic surfactants, silicone surfactants, gums, resins, dispersants, semicrystalline polymers, antioxidants, essential oils, preservatives, perfumes, neutralizing agents, antiseptics, anti-UV protective agents, cosmetic agents, such as vitamins, hydrating agents, emollients or collagen-protecting agents, and mixtures thereof.

A person skilled in the art can adjust the type and amount of additives present in the compositions according to the invention by means of routine operations, so that the cosmetic properties and the stability properties sought for these compositions are not affected by the additives.

Applications

The cosmetic compositions covered by the invention may be face or body treatment or makeup products or hair care products.

These compositions are thus intended to be applied onto the skin or hair.

The compositions of the invention can be conditioned in bottles of any type and of any shape commonly used for cosmetic products and more preferably in transparent bottles made of glass or plastic material such as polyethylene terephthalate (PET).

The invention is particularly well suited for bottles of which the walls are made of glass.

The present invention also relates to a non-therapeutic cosmetic skin treatment method comprising a step for applying at least one layer of a composition according to the invention onto the skin.

This invention also relates to a non-therapeutic makeup and/or skincare method comprising a step for applying at least one layer of a composition according to the invention onto the skin.

This invention also relates to a method for coating with keratin fibers comprising a step of application on said keratin fibers of a cosmetic composition according to the invention.

Throughout the application, the term "comprising a" or "including a" means "comprising at least one" or "including at least one", unless otherwise specified.

Throughout the above description, unless specified otherwise, the term "between x and y" refers to an inclusive range, i.e. the values x and y are included in the range.

EXAMPLES

Evaluation test of the Agglomeration of Nacres at Rest

In order to evaluate the agglomeration of nacres at rest, the following test is carried out in the framework of this invention:

A sample of 20 g of the composition is introduced into a bottle of about 30 mL (diameter 2.5 cm, height 8 cm).

In order to guarantee that the sample taken is true to the composition, it is conditioned after having homogenized the composition under shaking. The sample can as such be taken just after manufacture.

The bottle is allowed to rest for 24 hours in a vertical position, then it is agitated 10 times by energetic and vertical movements.

The agglomeration of the nacres is then judged:

If there is a complete re-homogenization of the nacres in the entire composition, the latter is in accordance with the invention, If the nacres remain agglomerated at the bottom of the bottle, or if the homogenization is only partial then the composition is not in accordance with the invention.

Examples 1 to 3

Influence of the Nature of the Substrate of the Nacre

Examples 1 to 3 make it possible to show the influence of the nature of the substrate of the nacre (particles (P1)) on the phenomenon of agglomeration at rest.

|   |   | mass % |
|---|---|---|
| A | Water | 10.50 |
|   | Absolute ethanol | 16.8998 |
|   | Propylene glycol | 25.20 |
|   | Glycerol | 16.90 |
|   | D&C Red No. 4 | 0.0001 |
| B | Isononyl isononanoate | 20.00 |
|   | D&C Violet No. 2 | 0.0001 |
| C | Nacre* | 10.50 |
|   | TOTAL | 100% |

*The nature of the nacre is mentioned in the table hereinbelow

Procedure

The compositions of the examples 1 to 3 are prepared according to the protocol described hereinafter.

The aqueous phase A is prepared separately by weighing the constituents in a beaker then by stirring using a bar magnet until homogenization.

The oily phase B is prepared separately in the same way.

The aqueous phase A is then introduced into the main beaker that is stirred using a dispersing turbine-Raynerie at a speed of 500 rpm.

The nacre (phase C) is then introduced in the aqueous phase under stirring so as to correctly homogenize.

Then the oily phase B is introduced into the beaker by maintaining under stirring.

The composition is stirred again for 15 min before conditioning.

| Examples | Nacres | Structure |
|---|---|---|
| Example 1 (Invention) (particles (P1)) | Mica-titanium oxide-brown iron oxide sold under the reference Pearlescent Pigment Flonac MX 30 C by Sudarshan Chemical | Mica/TiO$_2$/Iron ox. (82/14/4) |
| Example 2 (invention) (particles (P2)) | Silica-titanium oxide-tin oxide sold under the reference Xirona Magic Mauve by Merck | SiO$_2$/TiO$_2$/SnO$_2$ (88/10/2) |
| Example 3 (invention) (particles (P2)) | Calcium aluminum borosilicate-titanium oxide-tin oxide sold under the reference Metashine MC1080RR by Nippon Sheet Glass | Borosilicate/TiO$_2$/SnO$_2$ (78/21.5/0.5) |

It was therefore observed that nacre particles (P1) as described hereinabove in the description make it possible to obtain a composition in accordance with the invention, i.e. a three-phase composition at rest. In addition, in these compositions, the nacres are easily re-homogenized after stirring.

When the substrate is different from that of particles (P1) of the invention, this homogenization of nacres is not obtained in a manner that is as satisfactory.

The particles (P2) make it possible to obtain three-phase compositions but the compositions obtained are less advantageous in terms of properties of re-homogenization of nacres. These particles however make it possible to obtain advantageous compositions in terms of adhesion to the walls (cf. examples 15 and 16).

Examples 4 to 9

Variation in the Size

Examples 4 to 9 show the invention for nacres (P1) which contain a percentage of titanium dioxide less than or equal to 30%.

|  |  | mass % |
|---|---|---|
| A | Water | 10.50 |
|  | Absolute ethanol | 16.8998 |
|  | Propylene glycol | 25.20 |
|  | Glycerol | 16.90 |
|  | D&C Red No. 4 | 0.0001 |
| B | Isononyl isononanoate | 20.00 |
|  | D&C Violet No. 2 | 0.0001 |
| C | Nacre | 10.50 |
|  | TOTAL | 100% |

| Examples | Nacres | Structure | Average size | % TiO$_2$ | Aspect |
|---|---|---|---|---|---|
| Example 4 (Invention) | Mica-brown iron oxide sold under the reference Pearlescent Pigment Prestige soft bronze by Sudarshan Chemical | Mica/Iron. ox. (43/57) | 8 | 0 | Easy homogenization of the nacres after stirring |
| Example 5 (Invention) | Mica-titanium oxide-brown iron oxide sold under the reference Pearlescent Pigment Prestige soft beige by Sudarshan Chemical | Mica/TiO$_2$/Iron. ox./SnO$_2$ (41.8/20.2/37.8/0.20) | 8 | 20.2 | Easy homogenization of the nacres after stirring |
| Example 6 (Invention) | Synthetic mica (fluorphlogopite)-brown iron oxide sold under the reference Sunshine Glitter Russet by Sun Chemical | Synthetic mica/Iron. ox. (54.5/45.5) | 45 | 0 | Easy homogenization of the nacres after stirring |
| Example 7 (Invention) | Mica-brown iron oxide sold under the reference Pearlescent Pigment Flonac MX 30 C by Sudarshan Chemical | Mica/Iron. ox. (83/17) | 80 | 0 | Easy homogenization of the nacres after stirring |
| Example 8 (Invention) | Mica-titanium oxide-brown iron oxide sold under the reference Pearlescent Pigment Flonac MX 30 C by Sudarshan Chemical | Mica/TiO$_2$/Iron. ox. (82/14/4) | 97 | 14.0 | Easy homogenization of the nacres after stirring |
| Example 9 (Invention) | Synthetic mica (fluorphlogopite)-titanium oxide-oxide-iron oxide sold under the reference Sunshine Ultra Glitter Golden by Sun Chemical | Synthetic mica/TiO$_2$/Iron. ox. (82/14.5/3.5) | 230 | 14.5 | Easy homogenization of the nacres after stirring |

Procedure

The compositions of the examples 4 to 9 are prepared according to the protocol described hereinabove for the examples 1 to 3.

Sensory Evaluation

A panel of 4 women, aged 25 to 50, was asked to apply the example 4 as makeup on the face and the bust.

The results of this evaluation show that the product procures a pleasing makeup result as it is hardly pearly, it does not feel greasy or sticky.

Examples 10 to 12

Influence of the Percentage of Titanium

Examples 10 to 12 make it possible to show the influence of the size of the nacre (particles (P1)) when the percentage of titanium oxide of greater than 30%.

|   |   | mass % |
|---|---|---|
| A | Water | 10.50 |
|   | Absolute ethanol | 16.8998 |
|   | Propylene glycol | 25.20 |
|   | Glycerol | 16.90 |
|   | D&C Red No. 4 | 0.0001 |
| B | Isononyl isononanoate | 20.00 |
|   | D&C Violet No. 2 | 0.0001 |
| C | Nacre | 10.50 |
|   | TOTAL | 100% |

| Examples | Nacres | Structure | Average size | % $TiO_2$ | Aspect |
|---|---|---|---|---|---|
| Example 10 (Invention) | Mica-titanium oxide sold under the reference Timiron silk green by Merck | Mica/$TiO_2$/$SnO_2$ (31/68/1) | 12 | 68.0 | Easy homogenization of the nacres after stirring |
| Example 11 (Comparison) | Mica-titanium oxide-tin oxide sold under the reference Flamenco Summit Red R30D by BASF | Mica/$TiO_2$/$SnO_2$ (55.9/43.6/0.50) | 22 | 43.6 | Strong agglomeration of the nacres, homogenization is impossible |
| Example 12 (Comparison) | Mica-titanium oxide sold under the reference Flamenco Sparkle Green 820 J by BASF | Mica/$TiO_2$ (64/36) | 45 | 36.0 | Strong agglomeration of the nacres, homogenization is impossible |

Procedure

The compositions of the examples 10 to 12 are prepared according to the protocol described hereinabove for the examples 1 to 3.

It was therefore observed that the nacre particles as described hereinabove in the description (containing more than 30% by weight of titanium dioxide but with a size less than 20 μm) make it possible to obtain a composition in accordance with the invention, i.e. a three-phase composition at rest wherein the nacres are easily re-homogenized after stirring.

When the content of titanium dioxide is greater than 30% by weight and the size of the particles is greater than 20 μm, this homogenization of the nacres is not obtained in a satisfactory manner.

Examples 13 and 14

Variation in the Nature of the Oil

Examples 13 and 14 show the invention for different oils.

|   |   | mass % |
|---|---|---|
| A | Water | 10.50 |
|   | Absolute ethanol | 16.8998 |
|   | Propylene glycol | 25.20 |
|   | Glycerol | 16.90 |
|   | D&C Red No. 4 | 0.0001 |
| B | Oil | 20.00 |
|   | D&C Violet No. 2 | 0.0001 |
| C | Mica-brown iron oxide sold under the reference Pearlescent Pigment Flonac MX 30 C by Sudarshan Chemical | 10.50 |
|   | TOTAL | 100% |

| Examples | Oil | Aspect |
|---|---|---|
| Example 13 (Invention) | Dodecamethylpentasiloxane | Easy homogenization of the nacres |
| Example 14 (Invention) | Octyldodecanol | Easy homogenization of the nacres |

Procedure

The compositions of the examples 13 to 14 are prepared according to the protocol described hereinabove for the examples 1 to 3.

It was observed that the change in the nature of the oil according to examples 13 and 14 makes it possible to obtain compositions in accordance with the invention.

Evaluation Test of the Adherence of Nacres to the Walls

In order to evaluate the adherence of nacres to the walls, the following test is carried out in the framework of this invention:

A sample of 20 g of the composition is introduced into a glass bottle of about 30 mL (diameter 2.5 cm, height 8 cm).

In order to guarantee that the sample taken is true to the composition, it is conditioned after having homogenized the composition under shaking. The sample can as such be taken just after manufacture.

The bottle is allowed to rest for 24 hours in vertical position, before being evaluated.

The cleanliness of the walls of the bottle is then judged:
if the entire amount of the nacres is settled in the liquid medium, the latter is in accordance with the invention.
if a portion of the nacres is fixed to the walls of the bottle, then the composition is not in accordance with the invention.

Examples 15 to 17

Influence of the Nature of the Substrate of the Nacre

Examples 15 to 17 make it possible to show the influence of the nature of the substrate of the nacre (particles (P2)) on the phenomenon of adhesion to the walls.

|   |   | mass % |
|---|---|---|
| A | Water | 10.50 |
|   | Absolute ethanol | 16.8998 |
|   | Propylene glycol | 25.20 |
|   | Glycerol | 16.90 |
|   | D&C Red No. 4 | 0.0001 |
| B | Isononyl isononanoate | 20.00 |
|   | D&C Violet No. 2 | 0.0001 |
| C | Nacre | 10.50 |
|   | TOTAL | 100% |

Procedure

The aqueous phase A is prepared separately by weighing the constituents in a beaker then by stirring using a bar magnet until homogenization.

The oily phase B is prepared separately in the same way.

The aqueous phase A is then introduced into the main beaker that is stirred using a dispersing turbine-Raynerie at a speed of 500 rpm.

The nacre (phase C) is then introduced in the aqueous phase under stirring so as to correctly homogenize.

Then the oily phase B is introduced into the beaker by maintaining under stirring.

The composition is stirred again for 15 min before conditioning.

Adhesion of the Nacres to the Walls

Examples 15 and 16 correspond to the particles (P2) of the examples 2 and 3 hereinabove and the example 17 corresponds to the particles (P1) of the example 1 hereinabove.

It was therefore observed that nacre particles (P2) as described hereinabove in the description make it possible to obtain a composition in accordance with the invention, i.e. a three-phase composition at rest. In addition, in these compositions, the nacres are confined in the liquid medium and do not adhere to the walls of the bottle containing them.

When the substrate is different from that of the particles (P2) of the invention, the compositions are not as satisfactory in that the particles of nacres adhere to the walls of the bottle.

The particles (P1) make it possible to obtain three-phase compositions but the compositions obtained are less advantageous in terms of properties of adhesion of the nacres to the walls.

Sensory Evaluation

A panel of 4 women, aged 25 to 50, was asked to apply the example 2 as makeup on the face and the bust.

The results of this evaluation are that the product has a texture that is fine, slides and easy to work with.

Examples 18 to 21

Influence of the Position of the Layer of Silica

Examples 18 to 21 make it possible to show the influence of the position of the layer of silica of particles (P2) on the phenomenon of adhesion to the walls.

|   |   | mass % |
|---|---|---|
| A | Water | 10.50 |
|   | Absolute ethanol | 16.8998 |
|   | Propylene glycol | 25.20 |
|   | Glycerol | 16.90 |
|   | D&C Red No. 4 | 0.0001 |
| B | Isononyl isononanoate | 20.00 |
|   | D&C Violet No. 2 | 0.0001 |
| C | Nacre | 10.50 |
|   | TOTAL | 100% |

Procedure

The compositions of the examples 18 to 21 are prepared according to the protocol described hereinabove for the examples 1 to 3.

| Examples | Nacres | Structure | Aspect |
|---|---|---|---|
| Example 15 (invention) (particles (P2)) | Silica-titanium oxide-tin oxide sold under the reference Xirona Magic Mauve by Merck | $SiO_2/TiO_2/SnO_2$ (88/10/2) | Clean walls, nacres settled in the liquid medium |
| Example 16 (invention) (particles (P2)) | Calcium aluminum borosilicate-titanium oxide-tin oxide sold under the reference Metashine MC1080RR by Nippon Sheet Glass | Borosilicate/$TiO_2$/$SnO_2$ (78/21.5/0.5) | Clean walls, nacres settled in the liquid medium |
| Example 17 (invention - particles (P1)) | Mica-titanium oxide-brown iron oxide sold under the reference Pearlescent Pigment Flonac MX 30 C by Sudarshan Chemical | Mica/$TiO_2$/Iron ox. (82/14/4) | Presence of nacres on the walls of the bottle and in the liquid medium |

Adhesion of the Nacres to the Walls

| Examples | Nacres | Structure | Position of SiO2 layer | Aspect |
|---|---|---|---|---|
| Example 18 (Invention) | Mica-titanium oxide-silica sold under the reference Timiron splendid red by Merck | Mica/TiO$_2$/SiO$_2$ (33/55/12) | External | Clean walls, nacres settled in the liquid medium |
| Example 19 (Invention) | Mica-titanium oxide-silica sold under the reference Timiron artic silver by Merck | Mica/TiO$_2$/SiO$_2$ (46/40/14) | External | Clean walls, nacres settled in the liquid medium |
| Example 20 (Invention) | Mica-titanium oxide-Iron. ox.-silica-sold under the reference Colorona precious gold by Merck | Mica/TiO$_2$/Ox.fer/SiO$_2$ (35/24/20/20) | External | Clean walls, nacres settled in the liquid medium |
| Example 21 (Comparison) | Mica-titanium oxide-Silica-titanium oxide-tin oxide sold under the reference Xirona Glitter red gold by Merck | Mica/TiO$_2$/SiO$_2$/TiO$_2$/SnO$_2$ (62.5/19/17.5/1) | Internal | Presence of nacres on the walls of the bottle and in the liquid medium |

It was therefore observed that the nacre particles (P2) as described hereinabove in the description (containing mica as a substrate and an external layer of silica) make it possible to obtain a composition in accordance with the invention, i.e. a three-phase composition at rest wherein the nacres are confined in the liquid medium.

When the nacre particles (P2) contain mica as a substrate but no external layer of silica, then these nacre particles adhere to the walls of the bottle, which is not satisfactory according to the invention.

Example 22

Influence of the Percentage of Iron Oxide

Example 22, which is compared with example 15 (invention), makes it possible to show the influence of the percentage of iron oxide which, according to the invention, must be less than or equal to 50%.

|   |   | mass % |
|---|---|---|
| A | Water | 10.50 |
|   | Absolute ethanol | 16.8998 |
|   | Propylene glycol | 25.20 |
|   | Glycerol | 16.90 |
|   | D&C Red No. 4 | 0.0001 |
| B | Isononyl isononanoate | 20.00 |
|   | D&C Violet No. 2 | 0.0001 |
| C | Nacre | 10.50 |
|   | TOTAL | 100% |

Procedure

The compositions of the example 22 are prepared according to the protocol described hereinabove for the examples 15 to 17.

Adhesion of the Nacres to the walls

| Examples | Nacres | Structure | % iron oxide | Aspect |
|---|---|---|---|---|
| Example 15 (invention) | Silica-titanium oxide-tin oxide sold under the reference Xirona Magic Mauve by Merck | SiO2/TiO2/SnO2 (88/10/2) | 0 | Clean walls, nacres settled in the liquid medium |
| Example 22 (Comparative) | Silica-iron oxide sold under the reference Xirona Le Rouge by Merck | SiO2/Iron. Ox. (45/55) | 55 | Presence of nacres on the walls of the bottle and in the liquid medium |

It was therefore observed that the nacre particles (P2) as described hereinabove in the description (containing less than 50% by weight of iron oxide) make it possible to obtain a composition in accordance with the invention, i.e. a three-phase composition at rest wherein the nacres are confined in the liquid medium.

When the content in iron oxide is greater than 50% by weight, the nacres adhere to the walls of the bottle, which is not satisfactory according to the invention.

The invention claimed is:

1. Cosmetic composition comprising a physiologically acceptable medium containing:
   (1) an aqueous phase;
   (2) an oily phase with a density less than that of the aqueous phase; and
   (3) nacre particles, dispersed in the aqueous phase, constituted of a substrate partially or totally coated with one or more layers, with at least one of the layers being a layer of metal oxide,
       said nacre particles being chosen from the following particles:
       either nacre particles of which the average size is between 2 μm and 1,000 μm, wherein the substrate is mica or alumina,
       said particles do not comprise a silica layer on the surface, and
       with the proviso that, when the layer of metal oxide comprises more than 30% by weight of titanium oxide with respect to the total weight of the particles, the average size of said particles is between 2 μm and 20 μm;
       or nacre particles wherein the substrate is chosen from the comprising silica, borosilicate, mica and alumina, and when the substrate is mica or alumina, the nacre particles comprise a layer of silica on the surface, and
       when the metal oxide is an iron oxide, the iron oxide content is less than 50% by weight with respect to the total weight of the particles,
       said cosmetic composition comprising from 5% to 85% by weight of oily phase with respect to the total weight of said composition, and
       wherein said composition comprises at rest three visually separate phases.

2. Cosmetic composition according to claim 1, wherein the nacre particles have an average size between 2 μm and 1,000 μm,
   the substrate being mica or alumina,
   at least one of the layers being a layer of metal oxide,
   said particles do not comprise a silica layer on the surface, and
   with the proviso that, when the layer of metal oxide comprises more than 30% by weight of titanium oxide with respect to the total weight of the particles, the average size of said particles is between 2 μm and 20 μm,
   said cosmetic composition comprising from 5% to 70% by weight of oily phase with respect to the total weight of said composition.

3. Cosmetic composition according to claim 2, wherein the substrate of the particles is natural or synthetic mica.

4. Cosmetic composition according to claim 1, wherein the nacre particles are particles wherein at least one of the layers is a layer of metal oxide, and the substrate is chosen from the group comprising silica, borosilicate, mica and alumina,
   and wherein, when the substrate is mica or alumina, the nacre particles comprise a layer of silica on the surface, and
   when the metal oxide is an iron oxide, the iron oxide content is less than 50% by weight with respect to the total weight of the particles,
   said cosmetic composition comprising from 5% to 85% by weight of oily phase with respect to the total weight of said composition.

5. Cosmetic composition according to claim 4, wherein the substrate is borosilicate.

6. Cosmetic composition according to claim 1, comprising 0.1% to 30% by weight of nacre particles in relation to the total weight of said composition.

7. Cosmetic composition according to claim 1, wherein the metal oxides are chosen from the group comprising titanium oxide, iron oxides, chromium oxides, tin oxides, alumina oxides and mixtures thereof.

8. Cosmetic composition according to claim 1, wherein the substrate of the particles is coated with a single layer of metal oxide or several separate layers of metal oxide.

9. Cosmetic composition according to claim 1, wherein the nacre particles further comprise at least one layer constituted of bismuth oxychloride, ultramarine blue, Prussian blue, manganese violet, cochineal carmine and mixtures thereof.

10. Cosmetic composition according to claim 1, wherein the aqueous composition comprises 5% to 80% by weight of water with respect to the total weight of said composition.

11. Cosmetic composition according to claim 2, wherein the aqueous composition comprises 5% to 80% by weight of water with respect to the total weight of said composition.

12. Cosmetic composition according to claim 4, wherein the aqueous composition comprises 10% to 80% by weight of water with respect to the total weight of said composition.

13. Composition according to claim 1, wherein the aqueous phase comprises at least one organic solvent miscible in water.

14. Composition according to claim 1, wherein the oily phase comprises at least one oil chosen from the group comprised of hydrocarbon oils, silicone oils, fluorinated oils and mixtures thereof.

15. Non-therapeutic makeup and/or skincare method comprising a step for applying at least one layer of a composition according to claim 1 onto the skin.

16. Method for coating keratin fibers comprising a step for applying a cosmetic composition according to claim 1 onto said keratin fibers.

17. Cosmetic composition according to claim 2, comprising 0.1% to 30% by weight of nacre particles in relation to the total weight of said composition.

18. Cosmetic composition according to claim 3, comprising 0.1% to 30% by weight of nacre particles in relation to the total weight of said composition.

19. Cosmetic composition according to claim 4, comprising 0.1% to 30% by weight of nacre particles in relation to the total weight of said composition.

20. Cosmetic composition according to claim 5, comprising 0.1% to 30% by weight of nacre particles in relation to the total weight of said composition.

* * * * *